JUNIPER PLANT
Filed March 26, 1973 2 Sheets-Sheet 1
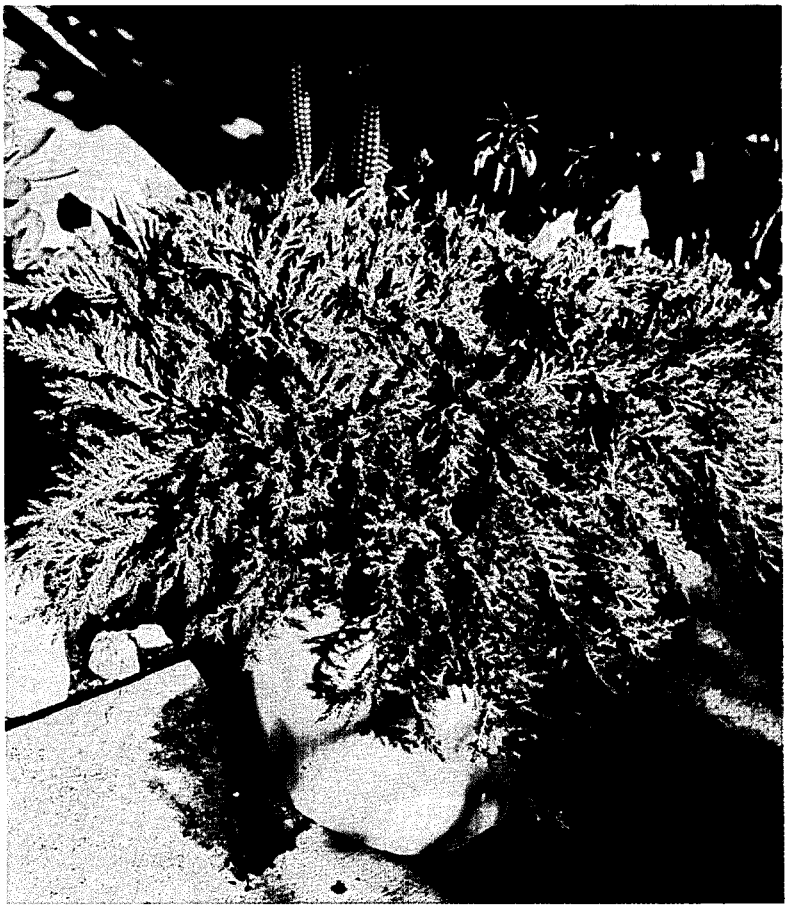

JUNIPER PLANT
Filed March 26, 1973 2 Sheets-Sheet 2
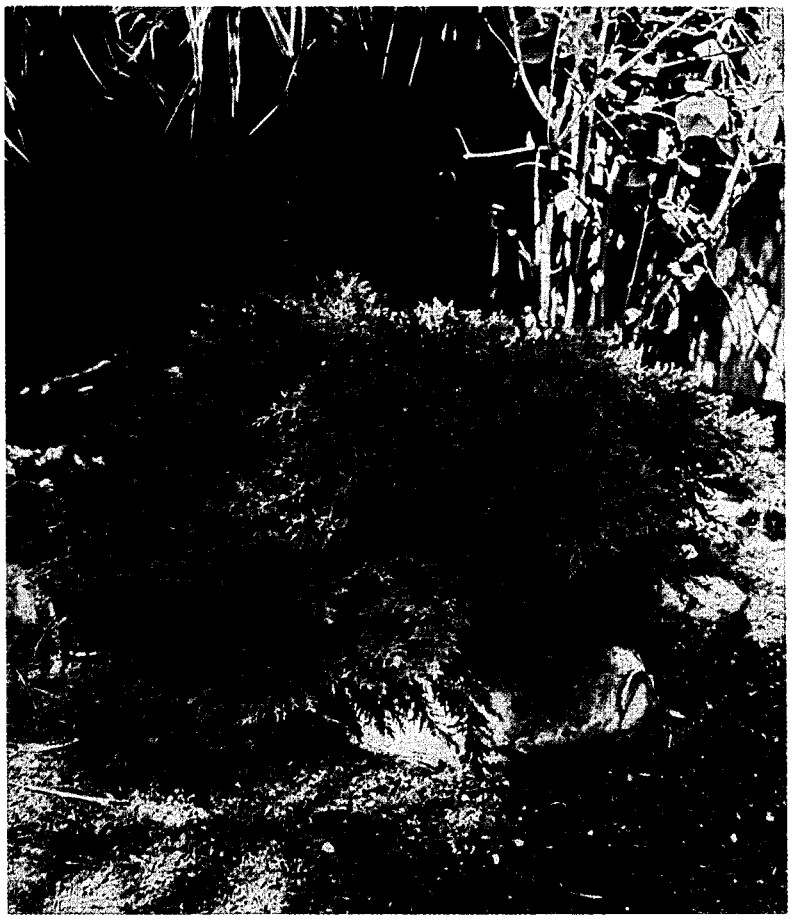

United States Patent Office

Plant Pat. 3,678
Patented Feb. 4, 1975

3,678
JUNIPER PLANT

Peter Mordigan, Sylmar, Calif., assignor to Select Nurseries, Inc., Brea, Calif.

Filed Mar. 26, 1973, Ser. No. 345,247
Int. Cl. A01h 7/00
U.S. Cl. Plt.—50 1 Claim

ABSTRACT OF THE DISCLOSURE

The present discovery relates to a new and distinct variety of ornamental plant of the Cupressaceae family and more specifically to a plant of the *Juniperus* genera.

---

The new variety was discovered by me as a sport on a plant in a group of Juniperus × media "Pfitzeriana," an unpatented variety, in 1937, growing on my property located at 12851 San Fernando Road, Sylmar, Calif. Original cuttings from the plant sport were grafted to Juniperus × media "Pfitzeriana" plants and the resulting plant differs so abruptly from the characteristics of Juniperus × media "Pfitzeriana" as to clearly distinguish it from its parent plant.

The new variety is a prostrate, evergreen, compact shrub that reaches a height of from 1½ feet to 2 feet, and has a spread of from three to four feet, making it suitable as a dwarf bush. The original plant bearing the sport has been known to attain a height of from 18 inches to 24 inches and a spread of from eight to ten feet. The leaves of the original plant bearing the sport are much wider and heavier than those of the new variety and are usually a dark green, the sport derivative is a bluish green.

The present variety has been asexually reproduced by me by means of cuttings. These plants are slow growing and take considerable time to attain the dimensions given above for the new variety.

This new variety has been asexually reproduced during the years since its discovery and these asexual reproductions have exhibited the characteristics set forth above. This clearly shows that the new variety has become well established.

The new variety has not been observed to produce any seed.

There are two accompanying drawings in full color, one of which is employed to show the juvenile foliage characteristic, and the other of which is employed to illustrate the Cyprus Green color of the new variety of dwarf prostrate juniper which has only juvenile leaves. The juvenile type of leaves are the only leaf form observed since the new variety was discovered. This plant retains its pleasant green coloration throughout the year and due to its prostrate habit of growth, small size, and slow growth, it makes an ideal ground covering plant for confined areas. It can also be grown in tubs and small containers.

The following is a detailed description of the new and distinct variety of Juniper. To assist in the identification of the important colors of the new variety, the nomenclature adopted by the British Horticultural Colour Charts has been followed.

THE PLANT

Locality where grown and observed: Sylmar, Calif.

General characteristics: The plant is a low, prostrate, compact, dwarf evergreen shrub that is ideal as a ground covering plant.

Branches: The plant is muchly branched and most of the branches are of fine caliper.

Trunk: The plant has a predominantly greyish brown trunk.

Foliage: The following foliage is present on the plant:

Juvenile:

*Size of leaves.*—The leaves vary from one-eighth to one-quarter of an inch in length and are quite narrow in width.

*Arrangement and form.*—The individual leaves are generally opposite and are 2 ranked. They later start spreading out somewhat but retain their needle-like shape. The tips of the leaves are spinescent. This juvenile leaf shape is the only form of leaf present regardless of the age of the plant, and this characteristic distinguishes the new variety from other species of prostrate Juniper × media "Pfitzeriana."

*Color.*—Cyprus Green 59/1.

*Texture.*—The leaves are stiff and spinescent. The juvenile form of leaves are best described as resinous.

Cones: No cones have been observed.

Seed: The plant has not borne seed to the present time.

I claim:

1. A new and distinct variety of juniper plant substantially as shown and described, characterized by its very dwarfed size, its hardy slow prostrate growth habit forming a tightly compact ground covering shrub, its thin needle-like Cyprus Green juvenile leaves which are present all of the time, the leaves being resinous in texture, and by the absence of cones and seed.

No references cited.

ROBERT E. BAGWILL, Primary Examiner